United States Patent
Ceccoli et al.

(10) Patent No.: US 10,449,129 B2
(45) Date of Patent: Oct. 22, 2019

(54) ENCAPSULATES OF SALICYLIC ACID AND POLYSALICYLIC ACID DERIVATIVES

(71) Applicant: Biocogent, LLC, Stony Brook, NY (US)

(72) Inventors: Joseph D. Ceccoli, Farmingville, NY (US); Michael L. Ingrassia, Hauppauge, NY (US); Christopher M. Judd, Riverhead, NY (US); Brian R. Costello, Port Jefferson Station, NY (US)

(73) Assignee: Biocogent, LLC, Stony Brook, NY (US)

( * ) Notice: Subject to any disclaimer, the term of this patent is extended or adjusted under 35 U.S.C. 154(b) by 108 days.

(21) Appl. No.: 15/552,032

(22) PCT Filed: Feb. 22, 2016

(86) PCT No.: PCT/US2016/018988
§ 371 (c)(1),
(2) Date: Aug. 18, 2017

(87) PCT Pub. No.: WO2016/134383
PCT Pub. Date: Aug. 25, 2016

(65) Prior Publication Data
US 2018/0036212 A1  Feb. 8, 2018

Related U.S. Application Data

(60) Provisional application No. 62/118,908, filed on Feb. 20, 2015.

(51) Int. Cl.
*A61K 8/14* (2006.01)
*A61K 8/85* (2006.01)
*A61Q 19/00* (2006.01)
*A61K 31/765* (2006.01)
*A61K 9/127* (2006.01)
*A61K 9/107* (2006.01)
*A61K 9/00* (2006.01)
(Continued)

(52) U.S. Cl.
CPC .............. *A61K 8/14* (2013.01); *A61K 8/11* (2013.01); *A61K 8/368* (2013.01); *A61K 8/85* (2013.01); *A61K 9/0014* (2013.01); *A61K 9/1075* (2013.01); *A61K 9/127* (2013.01); *A61K 31/765* (2013.01); *A61Q 19/00* (2013.01); *A61Q 19/007* (2013.01)

(58) Field of Classification Search
CPC .......... A61K 8/14; A61K 8/85; A61K 31/765; A61K 9/127; A61K 9/1075; A61K 9/0014; A61K 8/368; A61K 8/11; A61Q 19/007; A61Q 19/00
See application file for complete search history.

(56) References Cited

U.S. PATENT DOCUMENTS 5,411,742 A  5/1995  Sebag et al.
5,869,069 A  2/1999  Perrier et al.
(Continued)

*Primary Examiner* — Trevor Love
(74) *Attorney, Agent, or Firm* — Saul Ewing Arnstein & Lehr LLP; Domingos J. Silva

(57) ABSTRACT

The present technology relates to compositions comprising encapsulates, wherein the encapsulates include salicylic acid derivatives such as polysalicylic acid or its derivatives; as well as cosmetic, topical and pharmaceutical compositions comprising the same. The present technology provides improved compositions and systems comprising such compounds.

16 Claims, 2 Drawing Sheets

(51) Int. Cl.
*A61K 8/368* (2006.01)
*A61K 8/11* (2006.01)

(56) References Cited

U.S. PATENT DOCUMENTS

| | | |
|---|---|---|
| 6,540,987 B2 | 4/2003 | Weipert et al. |
| 2010/0221295 A1 | 9/2010 | Bovetto et al. |

ENCAPSULATES OF SALICYLIC ACID AND POLYSALICYLIC ACID DERIVATIVES

CROSS-REFERENCE TO RELATED APPLICATIONS

This application is a 35 U.S.C. § 371 National Stage application of, and claims priority to, International Patent Application Ser. No. PCT/US2016/018988, filed Feb. 22, 2016, which claims priority under 35 U.S.C. § 119(e) to U.S. Provisional Application Ser. No. 62/118,908, filed Feb. 20, 2015, all of which applications are incorporated herein by reference in their entireties.

BACKGROUND

The present technology relates to compositions comprising encapsulates, wherein the encapsulates include salicylic acid derivatives such as polysalicylic acid, resveratrol salicylate, NDGA salicylates and other derivatives thereof, as well as cosmetic, topical and pharmaceutical compositions comprising the same.

Encapsulation of active ingredients is useful as a method of preserving the integrity of the ingredients within a multi-ingredient composition after formulation but prior to use. Encapsulation technology includes, for example, liposomes and other structures, which are artificially prepared as vehicles for administration of active ingredients such as nutrients, cosmetics and pharmaceuticals.

Salicylic acid is an active ingredient often used in cosmetic and personal care products. While salicylic acid itself has been the subject of liposomal dispersions, the inclusion of salicylic acid derivatives, such as polysalicylic acid and its derivatives, has so far not been successful. Polysalicylic acid in particular presents challenges in encapsulation.

Thus, a need exists for improved methods of encapsulating such compounds, as well as compositions comprising such compounds.

SUMMARY OF THE DISCLOSED TECHNOLOGY

In certain embodiments, the present technology is directed to a composition comprising an encapsulate, the encapsulate comprising a salicylic acid derivative other than free salicylic acid.

In certain embodiments, the present technology is directed to a method of encapsulating a polysalicylic acid derivative, the method comprising the steps of: combining a hydrophilic carrier with a hydrophobic material or hydrophilic material; and subjecting the combination to high energy and high shear to produce an encapsulate.

In certain embodiments, the present technology is directed to a liposome delivery system for the containment and delivery of: (a) a salicylic acid derivative other than free salicylic acid; or (b) polysalicylic acid; the system comprising (a) or (b) in one or more liposome vesicles formed of lipidic bilayers, such that a first environment is formed in a core surrounded by the bilayers and a second environment is formed in a space external to the bilayers.

In certain embodiments, the present technology is directed to a liposome delivery system for the containment and delivery of: (a) a salicylic acid derivative other than free salicylic acid; or (b) polysalicylic acid; the system comprising (a) or (b) encapsulated within a micelle having a hydrophilic outer surface and a lipidic, internal hydrophobic environment, such that the encapsulated material is found within the lipidic, internal hydrophobic environment of the micelle.

DETAILED DESCRIPTION

Figure 1:
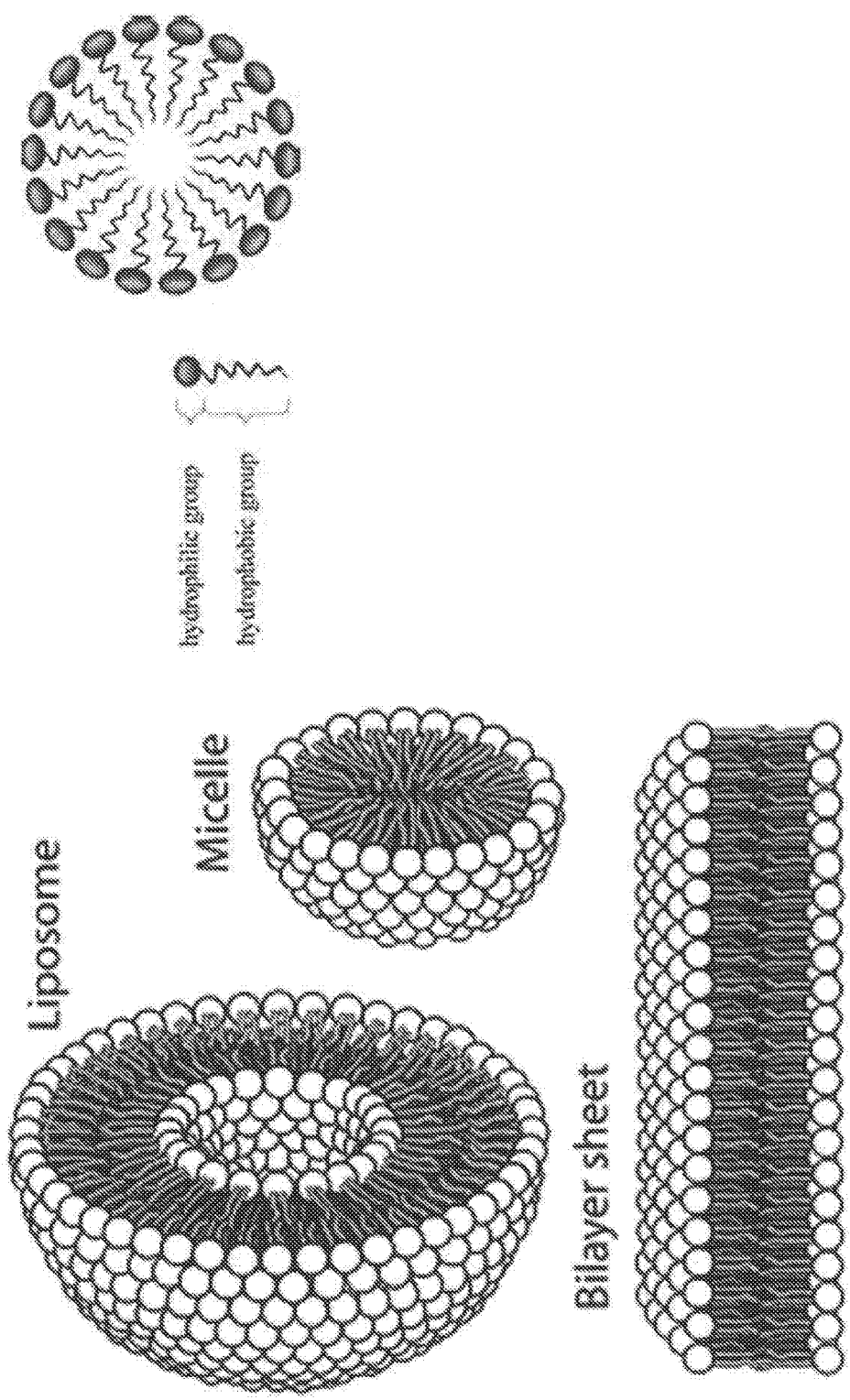
FIG. 1 shows the structure of a liposome, a micellar dispersion (also referred to interchangeably herein as a micelle), and a bilayer sheet as contemplated in certain embodiments herein. As can be seen, such structures typically are arranged according to the location of a hydrophilic group and a hydrophobic group of each element.

Salicylic acid is a commonly used ingredient in cosmetic and skin care applications, including exfoliation, hair and skin conditioning, treatment of dandruff and acne. Some derivatives of salicylic acid, including polysalicylic acid and its derivatives, exhibit many of the same benefits, but are advantageous in that the benefits are often even more pronounced. However these derivatives can be especially difficult to formulate due to their hydrophobicity and incompatibility with many solvents. Encapsulation assists in formulation and delivery or penetration of these materials to the user. In addition, encapsulation can contribute to enhanced product stability and facilitate sustained and safer delivery of salicylic acid and its derivatives via skin esterase activity.

Lastly, the ability to formulate salicylic acid polymers with larger chain lengths is beneficial due to their greater hydrophobicity, which further aids in skin permeation.

Described herein are novel and unique approaches to encapsulating salicylic acid and its derivatives, including polysalicylic acid, as well as to formulating cosmetic, topical and pharmaceutical compositions comprising such encapsulates.

As used herein, the term "salicylic acid" can include the salicylic acid molecule as well as derivatives thereof; the term "polysalicylic acid" can include the polysalicylic acid molecules—that is, any molecule comprising more than one salicylic moiety—as well as derivatives thereof. As used herein, the terms "salicylic acid alone," "SA alone, "free SA" and "free salicylic acid" are used interchangeably to mean the free salicylic acid molecule, not coupled to any other moiety.

For ease of reference, throughout the present disclosure, salicylic acid (including any derivatives thereof) may be referred to as "SA." Similarly, polysalicylic acid (including any derivatives thereof) may be referred to as "PSA."

As used herein, the term "salicylic acid derivative" or "derivatives thereof" (referring to salicylic acid) can include salicylic acid alone, and any other molecule that includes a salicylic acid moiety—for example, salicylates and compositions including polysalicylic acid and its derivatives.

As used herein, the term "polysalicylic acid derivative" or "derivatives thereof" (referring to polysalicylic acid) can include a molecule that has more than one salicylic acid moiety, including any molecule comprising two or more salicylate functional groups whether coupled to each other or whether coupled to another functional group.

As used herein, "essentially no salicylic acid alone," "essentially no free salicylic acid," "substantially free of free salicylic acid" and "substantially free of salicylic acid alone"

are used interchangeably to mean that the salicylic acid derivatives in a composition are essentially all in the form of PSA rather than free SA. That is, in various embodiments, such a composition contains less than about 5%, less than about 3%, less than about 2% or less than about 1% of free salicylic acid that is not coupled to another salicylic acid; the percentage being calculated as amount of free SA based on total PSA+free SA in the composition.

Put another way, in various embodiments, the compositions herein comprise encapsulates, wherein an encapsulate comprises at least about 95%, at least about 98% or at least about 99% of PSA; the percentage being calculated as amount of PSA based on total PSA+free SA in the composition. However, the technology herein also contemplates other embodiments wherein the mix of SA and PSA can be varied—for example, embodiments wherein an encapsulate comprises about 50 to about 99% of PSA, about 60 to about 99% of PSA, about 75 to about 99% of PSA or about 80 to about 99% of PSA; the percentage being calculated as amount of PSA based on total PSA+free SA in the composition.

SA and PSA derivatives as discussed herein may also refer to any molecule comprising SA or PSA conjugated with a target molecule, for example, any of the following:

Substituted or unsubstituted saturated monocarboxylic acids, such as acetic acid, propionic acid, butyric acid (C4), valeric acid, hexanoic acid, caprylic acid (C8), lauric acid, stearic acid (C18), isostearic acid (branched C18), linoleic acid, linolenic acid, myristic acid (C14), arachidic acid (C20), arachidonic acid, erucic acid, behenic acid (C22), lauric acid (C12), capric acid (C10), caproic (C6), and palmitic acid (C16); unsaturated monocarboxylic acids, such as acrylic acid, methacrylic acid, sorbic acid, oleic acid, linoleic acid, linolenic acid, docosahexaenoic acid, and eicosapentaenoic acid or any such acid C2 to C25 or greater;

Amino acids, such as Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Ornithine, Proline (also known as pyroglutamic acid), Selenocysteine, Serine, Tyrosine; as well as salts of any amino acids (for example, sodium pyroglutamate, or NaPCA);

Keto acids, such as pyruvic acid and acetoacetic acid;

Aromatic carboxylic acids, such as ascorbic acid, benzoic acid, salicylic acid, 2 and 3 furoic acid and ferulic acid; di- and tri-carboxylic acids, such as oxalic acid, malonic acid, malic acid, succinic acid, and glutaric acid.

Also suitable are carboxylic acids substituted with cyclic disulfide groups, e.g., lipoic acid. The designation "C" followed by a number indicates the number of carbon atoms in the alkyl chain.

In various embodiments, it may be desirable to include one or more botanical extracts or ferments in the compositions. If so, suggested ranges are about 0.0001 to about 10%, about 0.0005 to about 8%, about 0.001 to about 5%, about 0.01 to about 5%, about 0.01 to about 3%, about 0.01 to about 2% or about 0.01 to about 1% by weight of the total composition. Suitable botanical extracts include extracts from plants (including, e.g., from herbs, roots, flowers, fruits, vegetables, nuts, seeds, stems, leaves, pollen, nectar); for example, yeast ferment extract, *padica pavonica* extract, *thermus thermophilis* ferment extract, *camelina sativa* seed oil, *boswellia serrata* extract, olive extract, *aribodopsis thaliana* extract, *acacia dealbata* extract, *acer saccharinum* (sugar maple), acidophilus ferment extract, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, tea tree oil, chamomile, willowbark, mulberry, poppy, and any other type of botanical extract or ferment. Further examples include, but are not limited to, *Glycyrrhiza Glabra, Salix Nigra, Macrocycstis Pyrifera, Pyrus Malus, Saxifraga Sarmentosa, Vitis Vinifera, Moms Nigra, Scutellaria Baicalensis, Anthemis Nobilis, Salvia Sclarea, Rosmarinus Officianalis, Citrus Medica Limonum, Panax Ginseng*, and mixtures thereof.

Other useful target molecules include any of the following:

Sugars—including mono saccharides such as glucose, ribose, fructose, mannose, galactose; disaccharides such as sucrose, trehalose, maltose, cellobiose; polysaccharides such as gums, chitan; amino sugars and amino sugar derivatives such as Hyaluronic Acid and Chondroitin sulphates;

Lipids—including natural phospholipids, synthetic derivatives of phospholipids, fatty acids and derivatives, sterol lipids (including plant sterols such as sitosterol), ceramides, cholesterol or a combination thereof;

Polyphenolics—including tannins, ellagitanins, resorcinol, and other polyphenols, Organic Acids—including gallic acid, ursolic acid, hydrocinnamic acids such as ferulic acid, and heterocyclic carboxylic acid such as furoic acids;

Antioxidants—including ascorbic acid, Nordihydroguaiaretic acid (NDGA);

Flavones and flavonoids—including Quercetin, anthrocyanidins, hesperidin;

Vitamins—including A, B, C, D, E and K;

Amino acids—including Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Ornithine, Proline (also known as pyroglutamic acid), Selenocysteine, Serine, Tyrosine; as well as salts of any amino acids (for example, sodium pyroglutamate, or NaPCA).

Xanthines—including caffeine, theophylline and theobromine;

Mycosporine-like amino acids;

Enzymes—including glutathione S-transferases (GST's), superoxide dismutases (SOD), peroxidases, catalase; and Organic polymers—including dextran, polyglucosamine, polysaccharides, polyacrylates, polyvinylpyrrolidone.

All percentages discussed herein refer to weight percentages unless otherwise indicated. As used in the exemplary formulations herein, discussion of encapsulates of PSA can, in various embodiments, mean PSA in the absence of the SA molecule alone, or both PSA and SA.

As used herein, the terms "encapsulated" or "encapsulate" refer to any technology that involves the confinement of one or more individual molecules within a larger molecule or construct, or within a multi-lamellar structure, or coatings of one or more particles with another material. These include, but are not limited to, liposomes, micellar dispersions, reverse micelles and micellar dispersions, vesicles; encapsulates that are opened by breaking with force, including but not limited to shell encapsulates; encapsulates that are opened by dissolving in water or solvent, including but not limited to starch encapsulates; "reservoir type" encapsulates, including but not limited to capsules, single-core, mono-core or core-shell type encapsulates; "matrix type" encapsulates; "coated matrix type" encapsulates; nanocapsules, microcapsules, microreservoir encapsulates and the like, for example for not limited to, those structures shown in FIG. 1.

Figure 2:
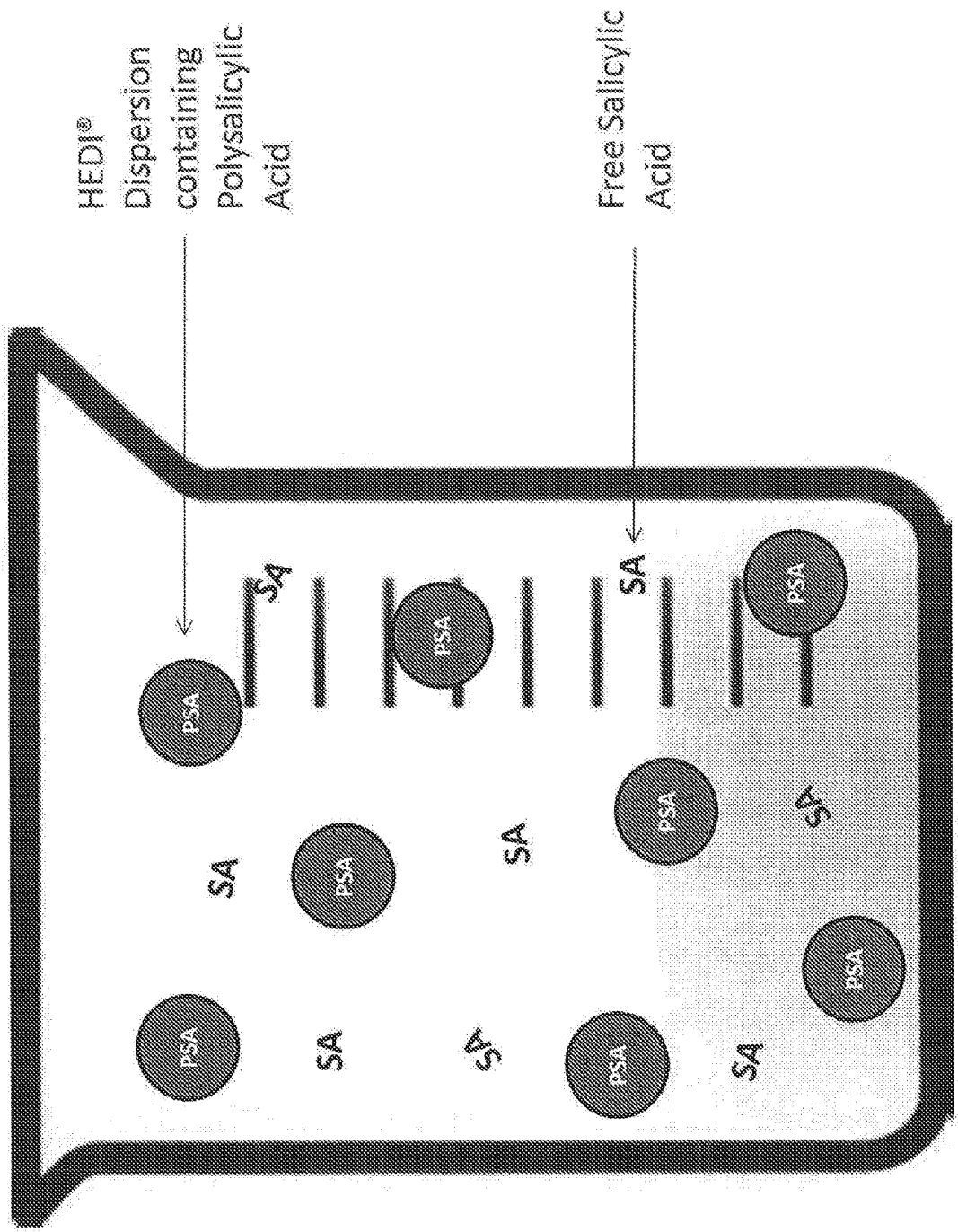
FIG. 2 shows a simplified description of the elements of a component of certain compositions herein. Free SA and PSA are shown in a dispersion, including but not limited to a high energy (e.g., HEDI™ dispersion).

In certain embodiments, the extracts herein may include one or more dispersion ingredients, including, for example, high energy dispersion ingredients (HEDI™ products). HEDI™ is a proprietary platform technology utilizing specialized, high-energy, high-shear process technology to generate unique chemical properties and the inclusion of hydrophilic and hydrophobic species together in a unified product, for example, as an emulsion. Briefly, hydrophilic carriers (e.g., aqueous systems) are combined with hydrophobic materials (e.g., polysalicylic acid) or sparingly hydrophilic materials (e.g., salicylic acid) and emulsifying agents, amphiphilic materials, polymers such as phospholipids or polyethylene glycol, e.g., acrylic acid polymers such as Carbomer 672, 690, 910, 934, 934P, 940, 941; or the like which are then are subjected to the HEDI™ or other processes yielding stable micellar or multi-lamellar structures, in which materials are trapped internally in the hydrophobic phase of the vesicles. An exemplary dispersion is shown in FIG. 2.

SA is nearly insoluble in water (having a limit of solubility of approximately 0.2 percent at room temperature). PSA is similarly water insoluble, and in fact is not soluble in most solvents that are used in cosmetics; at least for this reason, formulation and encapsulation of PSA is difficult. The insolubility issues associated with the SA molecule alone are generally expected to be compounded with the PSA molecule, at least for the reason that the PSA molecule is larger and therefore expected to be even less soluble than free SA. Thus, the PSA molecule has not been expected to be useful for many uses including cosmetic and personal care applications, as it is generally difficult to incorporate into compositions and mixtures.

Shown below is a Table of results from a study of the solubility of polysalicylic acid in various solvents. In the Table, a minus sign (−) indicates no measurable solubility; a plus sign (+) indicates measurable solubility.

TABLE 1

| Solvent | 10% PSA | 5% PSA |
|---|---|---|
| 50 mM Tris, 150 mM NaCl pH 8.5 | − | − |
| 50:50 Glycerine:H2O | − | − |
| Isopropyl Palmitate | − | − |
| propylene glycol diethylhexanoate | − | −(some solubility, hazy) |
| Butylene Glycol | − | − |
| Capric/Caprylic Triglycerides | − | − |
| Polyethylene glycol | + | + |
| Isostearic Acid | − | − |
| Glycerine | − | − |
| Olive oil | − | − |
| Squalane | − | − |
| High Oleic Sunflower Oil | − | − |
| Propylene glycol caprylate | − | +(worked with heat (20 min @ 37 C.)) |

U.S. Pat. No. 5,585,109 to Hayward et al. discusses encapsulation of salicylic acid alone, but does not teach derivatives of salicylic acid including polysalicylic acid. In certain embodiments described herein, a polysalicylic acid molecule or set of molecules can be encapsulated in the lipidic portion of a liposome, and not in any aqueous portion of the liposome; or in small and insignificant amounts in the aqueous portion of the liposome; e.g., less than about 10%, less than about 5%, less than about 3% or less than about 1% based on the total amount of polysalicylic acid molecule present in the entire system. Further, in certain embodiments described herein, a polysalicylic acid molecule or set of molecules or derivatives can be encapsulated in a micelle. Hayward does not teach or suggest encapsulation in micelles, as Hayward discusses the fact that the internal surfaces of the liposome are hydrophilic (rather than hydrophobic, which is the case with the internal environment of a micelle). Thus, Hayward teaches away from encapsulation of SA in a micelle.

In certain embodiments the technology described therein focuses on encapsulating a salt of SA, a PSA or a salt of PSA in water, thus increasing water solubility. PSA is not water soluble, and in fact, is not soluble in most solvents that are commonly used in cosmetics. Thus, the general ability to encapsulate the PSA molecule, as well as the ability to encapsulate the PSA molecule in either lipid or water, are among the many unexpected benefits of the present technology.

In various embodiments, a composition herein may comprise any of the following: (a) PSA encapsulated with no other SA in the composition; (b) PSA encapsulated with SA alone elsewhere in the composition but not encapsulated; (c) PSA and SA combined together and encapsulated together in the composition.

In certain embodiments, the PSA is contained within a micellar dispersion or reverse micellar dispersion or liposome, other lamellar structures or a proliposome. In certain embodiments herein, the compositions herein comprise polysalicylic acid encapsulated in a high energy dispersion, and optionally salicylic acid contained in the continuous phase, such that the polysalicylic acid is "encapsulated" but the salicylic acid is present, but not encapsulated, in the milieu that carried the PSA (for example, water), as shown for example in FIG. 2.

In certain embodiments, an encapsulate according to the technology herein comprises a lipidic bilayer that forms a lipidic, hydrophobic environment surrounding an aqueous core. In certain embodiments, a portion or all of the salicylic acid derivative other than the salicylic acid molecule (for example, PSA or a derivative of PSA) is located within the lipidic, hydrophobic environment of the liposomal bilayers. The system can comprise the salicylic acid derivative in one or more liposome vesicles formed of lipidic bilayers, such that a first environment is formed in a core surrounded by the bilayers and a second environment is formed in a space external to the bilayers.

In certain embodiments, the lipidic bilayers are such that a first environment is formed in a space surrounded by said bilayers and a second environment is formed in a space external to said bilayers; wherein substantially all said salicylic acid present in said system is present external to said liposome vesicles. The pH of the two environments could be essentially the same or different. That is, in certain embodiments, the pH of the first environment may be maintained in a state that is essentially the same as that of the second environment (e.g., two values having a difference of less than a half unit of pH); or the pH of said first environment may be maintained in a state that is distinct from that state of said second environment (e.g., two values having a difference of greater than or equal to a half unit of pH). For example, if the first environment has a pH of 7, and the second environment has a pH of 7.3, the two environments would have essentially the same pH as defined herein. In various embodiments, the pH difference between the two environments (measured by comparing the pH units on the pH scale of 1 to 14) can be about 0.5 to about 13 pH units, about 0.5 to about 12 pH units, about 1 to about 12 pH units, about 1 to about 10 pH units, about 1 to about 8 pH units, about 1 to about 5 pH units, about 1 to about 3 pH units, about 0.5 to about 3 pH units or about 0.5 to about 2 pH units.

In certain embodiments, an encapsulate according to the technology herein comprises a micelle having an internal hydrophobic environment and an external hydrophilic environment (as seen, for example in FIG. 1). In such a case, the pH of the solution outside of the micelle can be, in various embodiments, about 1 to about 12, about 2 to about 10, about 3 to about 9, about 4 to about 9, about 5 to about 9, about 5 to about 8, about 5 to about 7 or about 6 to about 7.

In certain embodiments, technology herein is directed to a system encapsulated within a micelle having a hydrophilic outer surface and a lipidic, internal hydrophobic environment, such that all the encapsulated material is found within the lipidic, internal hydrophobic environment of the micelle.

In certain embodiments, the compositions discussed herein can include any other suitable cosmetic or pharmaceutical ingredients, for example, any one or more of the following: solvents; acids, bases, water, colorants (including pigments or dyes), humectants (e.g., propylene glycol, hexylene glycol, butylene glycol, glyceryl triacetate, neoagarobiose, sugar alcohols, polymeric polyols, urea, quillaia, aloe vera gel, MP diol, lactic acid, honey or lithium chloride), emollients, moisturizing agents, sunscreen agents, anti-inflammatory agents, vitamins (e.g., tocopheryl acetate also known as Vitamin E acetate or retinyl palmitate also known as Vitamin A palmitate), minerals, germicides, antibacterial agents, antiviral agents, sterols and other lipids; surfactants, whether ionic, nonionic or anionic; solvents, whether organic or inorganic (including water or alcohol), humectants (e.g., propylene glycol, hexylene glycol, butylene glycol, glyceryl triacetate, sorbitol, neoagarobiose, sugar alcohols, polymeric polyols, urea, quillaia, aloe vera gel, MP diol, lactic acid, honey or lithium chloride), drying agents or desiccants (e.g., activated alumina, aerogel, benzophenone, bentonite clay, calcium chloride, calcium sulfate, cobalt(II) chloride, copper(II) sulfate, lithium chloride, lithium bromide, magnesium sulfate, magnesium perchlorate, potassium carbonate, silica gel, sodium chlorate, sodium chloride, sodium hydroxide, sodium sulfate or a sugar), wetting agents, dispersants, plasticizers, detergents, emulsifiers (for example, lecithin), preservatives (for example, Phenoxyethanol (and) Methylparaben (and) Ethylparaben (and) Butylparaben (and) Propylparaben (and) Isobutylparaben, known as Phenonip®); as well as any other suitable cosmetic or skin care ingredients that further render such compositions suitable for application to the skin or hair.

In certain embodiments, pigments include but are not limited to: calcium oxide, barium oxide, aluminum oxide, iron oxides, titanium dioxide or mica.

In certain embodiments, the compositions discussed herein may include, or be included in other compositions that also include one or more agents for treating or ameliorating any of the following: skin conditions including but not limited to acne, pimples, rosacea, wrinkles or fine lines or the appearance thereof, sunburn, sun damage, eczema, psoriasis, scarring, dandruff, dry skin or dry scalp, allergic reactions or inflammation. As used herein, "treating" and "ameliorating" mean alleviating or improving a symptom, subjective or objective sensation, or subjective or objective appearance of any condition; regardless of the degree of alleviation or improvement.

Products created using the technology described in this application can be included as ingredients in any of various types of cosmetic, personal care, veterinary or pharmaceutical formulations, including but not limited to: creams, blush, lotions, serums, foundation makeup, powders, eyeshadow, eyeliner, mascara, lip color (e.g., lipstick and lipbalm), ointments, salves, unguents, balms, gels, oils, foams, masks, soaps, body washes, shampoos, hair conditioners, sunscreen, astringents, exfoliating agents, deodorants, treatments for acne, pimples, warts, eczema, rosacea; fungal treatments, nail treatments and colorants, sunburn treatments, colloids, hydrocolloids, sterols, lipids, facial peels and the like.

Exemplary agents for treating dandruff include, but are not limited to: selenium, selenium salts, resorcinol, alcohol, astringents and coal tar. Exemplary agents for treating acne include, but are not limited to: benzoyl peroxide and resorcinol. Exemplary germicides or antimicrobials include, but are not limited to: parabens, chlorphenesin, kathon CG, phenoxyethanol and germall 115.

Exemplary sunscreens include, but are not limited to: octyl methoxycinnimate and butyl methoxydibenzoylmethane (avobenzone); and cyanodiphenylacrylate ("crylene") polymer compounds including monocrylene, polycrylene and methoxycrylene. Exemplary emollients include, but are not limited to: silicones, glycerin and lanolin and lanolin derivatives. Exemplary hydrocolloids include, but are not limited to: hyaluronic acid, guar, carrageenan, alginic acid, polyacrylates, polymethacrylates and polyethylene glycols (PEGs) and their derivatives. Exemplary vitamins include, but are not limited to: vitamin E, vitamin A, vitamin A palmitate, vitamin B, vitamin K and Vitamin C.

Exemplary sterols include, but are not limited to: sitosterol, stigmasterol, phytosterols and cholesterol. Exemplary lipids include, but are not limited to: ceramides, cerebroside and other sphingolipids In various embodiments, it may be desirable to include one or more extracts in the compositions, including but not limited to botanical extracts. If so, suggested ranges are about 0.0001 to about 10%, about 0.0005 to about 8% or about 0.001 to about 5% by weight of the total composition. Suitable extracts include extracts from plants (herbs, roots, flowers, fruits, vegetables, seeds, leaves, pollen, nectar), bacteria and fungi; for example, yeast ferment extract, *Padica pavonica* extract, *Thermus thermophilis* ferment extract, *Camelina sativa* seed oil, *Boswellia serrata* extract, olive extract, *Arabidopsis thaliana* extract, *Acacia dealbata* extract, *Acer saccharinum* (sugar maple), acidophilus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and any other type of botanical extract Further examples include, but are not limited to, *Glycyrrhiza glabra, Salix nigra, Macrocycstis pyrifera, Pyrus malus, Saxifraga sarmentosa, Vitis vinifera, Moms nigra, Scutellaria baicalensis, Anthemis nobilis, Salvia sclarea, Rosmarinus officianalis, Citrus medica limonum, Panax ginseng*, and mixtures thereof.

Compositions incorporating the present technology may also include any of the following:

Sugars—including mono saccharides such as glucose, ribose, fructose, mannose, galactose; disaccharides such as sucrose, trehalose, maltose, cellobiose; polysaccharides such as gums, chitan; amino sugars and amino sugar derivatives such as Hyaluronic Acid and Chondroitin sulphates;

Lipids—including natural phospholipids, synthetic derivatives of phospholipids, fatty acids and derivatives, sterol lipids, ceramides, cholesterol or a combination thereof.

Polyphenolics—including tannins, ellagitanins, resorcinol, and other polyphenols, Organic Acids—including gallic acid, ursolic acid, hydrocinnamic acids such as ferulic acid, and heterocyclic carboxylic acid such as furoic acids;

Antioxidants—including ascorbic acid, Resveratrol and Nordihydroguaiaretic acid (NDGA);

Flavones and flavonoids—including Quercetin, anthrocyanidins, hesperidin;

Vitamins—including A, B, C, D, E and K;

Amino acids—including Histidine, Alanine, Isoleucine, Arginine,

Leucine, Asparagine, Lysine, Aspartic acid, Methionine, Cysteine, Phenylalanine, Glutamic acid, Threonine, Glutamine, Tryptophan, Glycine, Valine, Ornithine, Proline, Selenocysteine, Serine, Tyrosine;

Xanthines—including caffeine, theophylline and theobromine;

Mycosporine—like amino acids;

Enzymes—including glutathione S-transferases (GST's), superoxide dismutases (SOD), peroxidases, catalase; and Organic polymers—including dextran, polyglucosamine, polysaccharides, polyacrylates, polyvinylpyrrolidone.

In certain embodiments, an encapsulate as discussed herein may be in any form that can be delivered to the skin or mucosa of a user, or can be ingested by a user internally. These include, for example, a pill, tablet, caplet, capsule, dragee, sachet, lotion, liquid, foam, gel, suspension, infusion, suppository, cream, a lipstick or lipbalm, dissolvable strip, patch, paste, solid or semisolid.

In certain embodiments, an exemplary formulation in accordance with the present technology comprises: (a) about 0.5 to about 10% by weight of a membrane-forming lipid phase; (b) about 0.5 to about 25% by weight of SA or PSA; (c) about 0.5 to about 25% by weight of a water-soluble organic base; (d) about 40 to about 98.5% by weight of water or any solvent. In certain embodiments, a formulation further comprises (e) about 0.5 to about 30% by weight of other suitable cosmetic, pharmaceutical or topical ingredients as discussed herein.

In another embodiment, a composition of the present technology comprises:
a) about 1 to about 4% by weight of a membrane-forming lipid phase;
b) about 5 to about 12% by weight of SA or PSA;
c) about 2 to about 15% by weight of a water-soluble organic base;
d) about 60 to about 90% by weight of water; and
e) about 5 to about 15% by weight of other suitable cosmetic ingredients, including one or more of a solvent, a surfactant, an emollient, an emulsifier, a humectant, a colorant, an antimicrobial, water, a preservative or a vitamin.

In another embodiment, a composition of the present technology comprises:
a) about 0.5 to about 10% by weight of a membrane-forming lipid phase;
b) about 0.05 to about 20% by weight of PSA;
c) about 0.05 to about 25% by weight of a water-soluble organic base; and
d) about 40 to about 99.9% by weight of water.

In another embodiment, the present technology comprises a cosmetic composition for the containment and delivery of polysalicylic acid, comprising:
a) a liposome, said liposome comprising one or more lipidic bilayers that form a lipidic, hydrophobic environment surrounded by an aqueous core:
b) polysalicylic acid localized within the lipidic, hydrophobic environment of the one or more lipidic bilayers;
a) membrane-impermeant, water-soluble organic base; and
d) water, wherein an amount of said base may be varied within said composition thereby varying its pH without affecting said salicylic acid localized within said lipidic, hydrophobic environment.

In another embodiment, the present technology comprises a composition comprising:
a) about 0.1% to about 10% by weight of a lipid phase structurally arranged to form liposomal bilayer vesicles;
b) about 0.05% to about 20% by weight of polysalicylic acid;
c) about 0.05% to about 25% by weight of a water-soluble organic base;
d) about 40% to about 99.8% by weight of water;
e) about 0.01% to about 20% by weight of cosmetic ingredients;

In certain embodiments, the compositions and methods herein relate to the formation of encapsulates through any methods, including but not limited to the following: spray drying, agglomeration, granulation, pressure agglomeration, compaction, fluid bed coating, spray-chilling/cooling, melt injection, melt extrusion, emulsification, preparation of emulsions with multilayers, coacervation, preparation of microspheres via extrusion or dropping or emulsification, preparation of emulsions with protein or biopolymer multilayers, co-extrusion, inclusion complexation, liposome entrapment, rapid expansion of supercritical fluid (RESS), freeze-drying, vacuum-drying, preparation of nanoparticles, encapsulation through supercritical fluid technology.

In certain embodiments, the compositions and methods herein relate to micellar constructs comprising spherical or liquid crystalline "sheets" that hold a hydrophobic payload in an aqueous continuous phase.

Example 1 (PSA Composition)

An exemplary formulation can be prepared, with the weight percentages within the final product as follows:
about 0.5 to about 3% emulsifier;
about 80 to about 90% water;
about 5 to about 20% PSA;
optionally about 0.5 to about 2% preservative;
optionally about 0.5 to about 2% vitamin; and
about 1 to about 10% amino acid.

Example 2 (Moisturizing)

An exemplary formulation can be prepared, with the weight percentages within the final product as follows:
about 0.5 to about 5% emulsifier;
about 0.2 to about 1% plant sterol;
about 75 to about 90% water;
about 0.5 to about 2% amino acid salt;
about 1 to about 10% PSA;
optionally about 0.5 to about 2% preservative;
optionally about 1 to about 3% vitamin; and
about 1 to about 10% amino acid.

Example 3 (Anti-Acne)

An exemplary formulation can be prepared, with the weight percentages within the final product as follows:
about 1 to about 3% emulsifier;
about 0.1 to about 3% sterol;
about 1 to about 10% one or more amino acids;
about 0.01 to about 1% polyphenolic;
about 2 to about 10% PSA;
about 1 to about 5% antimicrobial agent;

about 0.5 to about 2% sugar;
about 75 to about 90% water.

Example 4 (Moisturizing Gel)

An exemplary formulation can be prepared, with the weight percentages within the final product as follows:
about 1 to about 3% emulsifier;
about 0.5 to about 2% amino acid salt;
about 1 to about 10% PSA; about 1 to about 5% antimicrobial.
about 0.1 to about 3% amino acid.
about 1 to about 5% humectant; and
about 0.1 to about 2% acrylic acid polymer.

In summary, the embodiments of the present technology are highly superior for many reasons, including but not limited to the following: there does not currently exist a useful mechanism for encapsulating PSA, either alone or in combination with SA. The synthetic approaches and subsequent purification methods used herein are unexpectedly lead to stable products that show superior results, can avoid toxic and mutagenic solvents, and are highly amenable to scaleup.

Although the present technology has been described in relation to particular embodiments thereof, these embodiments and examples are merely exemplary and not intended to be limiting. Many other variations and modifications and other uses will become apparent to those skilled in the art. The present technology should, therefore, not be limited by the specific disclosure herein, and may be embodied in other forms not explicitly described here, without departing from the spirit thereof.

What is claimed:

1. A composition comprising an encapsulate comprising polysalicylic acid or a salt thereof wherein the encapsulate is a liposome, micellar dispersion, or bilayer sheet.

2. The composition of claim 1, wherein the encapsulate is substantially free of free salicylic acid.

3. The composition of claim 1, wherein the encapsulate comprises a lipidic bilayer that forms a lipidic; hydrophobic environment within which at least a portion of the polysalicylic acid is located.

4. The composition of claim 1, wherein the encapsulate comprises a micelle that forms a lipidic internal hydrophobic environment within which at least a portion of the polysalicylic acid is located.

5. The composition of claim 1, further comprising one or more dispersion ingredients.

6. The composition of claim 1, further comprising salicylic acid.

7. The composition of claim 1, wherein the encapsulate comprises at least about 95% polysalicylic acid.

8. The composition of claim 1, which is formulated as a skin care or cosmetic formulation.

9. The composition of claim 1, further comprising one or more of the following: a solvent, a surfactant, an emollient, an emulsifier, a humectant, a colorant, an antimicrobial, water, a preservative, or a vitamin.

10. A liposome delivery system for the containment and delivery of polysalicylic acid; the system comprising polysalicylic acid encapsulated in a liposome vesicles formed of lipidic bilayers.

11. A liposome delivery system for the containment and delivery of polysalicylic acid; the system comprising polysalicylic acid encapsulated in a micelle having a hydrophilic outer surface and a lipidic, internal hydrophobic environment, such that the encapsulated polysalicylic acid is within the lipidic, internal hydrophobic environment of the micelle.

12. A skin care or cosmetic composition comprising the liposome delivery system of claim 10.

13. A skin care or cosmetic composition comprising the liposome delivery system of claim 11.

14. The composition of claim 1, further comprising an ingredient selected from the group consisting of a solvent, a surfactant, an emollient, an emulsifier, a humectant, a colorant, an antimicrobial, water, a preservative, and a vitamin.

15. The composition of claim 1, comprising:
a) about 1 to about 4% by weight of a membrane-forming lipid phase;
b) about 5 to about 12% by weight of polysalicylic acid;
c) about 2 to about 15% by weight of a water-soluble organic base;
d) about 60 to about 90% by weight of water; and
e) about 5 to about 15% by weight of other suitable cosmetic ingredients comprising one or more of a solvent, a surfactant, an emollient, an emulsifier, a humectant, a colorant, an antimicrobial, water, a preservative, or a vitamin.

16. The composition of claim 1, comprising:
a) about 0.5 to about 10% by weight of a membrane-forming lipid phase;
b) about 0.05 to about 25% by weight of polysalicylic acid;
c) about 0.05 to about 25% by weight of a water-soluble organic base; and
d) about 40 to about 98.5% by weight of water.

* * * * *

UNITED STATES PATENT AND TRADEMARK OFFICE
CERTIFICATE OF CORRECTION

PATENT NO. : 10,449,129 B2
APPLICATION NO. : 15/552032
DATED : October 22, 2019
INVENTOR(S) : Joseph D. Ceccoli et al.

Page 1 of 1

It is certified that error appears in the above-identified patent and that said Letters Patent is hereby corrected as shown below:

In the Specification

In Column 4, Line 15:
Please replace the word "chitan" with -- chitosan --.

In Column 8, Line 57:
Please replace the word "chitan" with -- chitosan --.

Signed and Sealed this
Eleventh Day of February, 2020

Andrei Iancu
*Director of the United States Patent and Trademark Office*